(12) United States Patent
Krol et al.

(10) Patent No.: US 7,203,386 B2
(45) Date of Patent: Apr. 10, 2007

(54) SELF-REFERENCING WAVEGUIDE GRATING SENSORS

(75) Inventors: Mark F. Krol, Painted Post, NY (US); Mark D. Salik, Montgeron (FR)

(73) Assignee: Corning Incorporated, Corning, NY (US)

( * ) Notice: Subject to any disclaimer, the term of this patent is extended or adjusted under 35 U.S.C. 154(b) by 323 days.

(21) Appl. No.: 10/947,021

(22) Filed: Sep. 21, 2004

(65) Prior Publication Data

US 2006/0062509 A1 Mar. 23, 2006

(51) Int. Cl.
*G02B 6/00* (2006.01)
*G02B 6/34* (2006.01)
*G01N 33/53* (2006.01)
*G01N 21/00* (2006.01)

(52) U.S. Cl. .................. 385/12; 385/37; 385/129; 356/246; 422/58; 422/82.11; 422/102; 435/7.1

(58) Field of Classification Search .............. 385/12, 385/37, 129; 356/246; 422/58, 68.1, 102, 422/82.11; 435/7.1
See application file for complete search history.

(56) References Cited

U.S. PATENT DOCUMENTS

| | | | |
|---|---|---|---|
| 4,815,843 A | 3/1989 | Tiefenthaler et al. | 356/128 |
| 6,455,004 B1 | 9/2002 | Tiefenthaler | 422/91 |
| 2002/0127565 A1 | 9/2002 | Cunningham et al. | 435/6 |
| 2002/0168295 A1 | 11/2002 | Cunningham et al. | 422/82.05 |
| 2003/0017580 A1 | 1/2003 | Cunningham et al. | 435/287.2 |
| 2003/0017581 A1 | 1/2003 | Li et al. | 435/287.2 |
| 2003/0026891 A1 | 2/2003 | Qiu et al. | 427/58 |
| 2003/0027327 A1 | 2/2003 | Cunningham et al. | 435/287.2 |

(Continued)

OTHER PUBLICATIONS

M.D. Salik et al., "Resonant Excitation Analysis of Waveguide Grating Couplers", Optics Communications, vol. 193, 2001, pp. 127-131.

(Continued)

*Primary Examiner*—Frank G. Font
*Assistant Examiner*—Michael P. Mooney
(74) *Attorney, Agent, or Firm*—William J. Tucker; Thomas R. Beall

(57) ABSTRACT

Self-referencing optical sensors and methods are described herein that can be used to detect bio-chemical interactions (e.g., biological binding of antigen-antibody pairs) that occur in for example a microplate. In one embodiment, the self-referencing optical sensor includes a substrate, a lower (reference) waveguide grating structure, a buffer layer and an upper (sensing) waveguide grating structure. This self-referencing optical sensor enables an optical interrogation system to detect a bio-chemical interaction independent of the effect of temperature by measuring a reference signal associated with the lower (reference) waveguide grating structure and measuring a sensing signal associated with the upper (sensing) waveguide grating structure. These two signals are then subtracted from one another to determine a sensing measurement that represents whether or not the bio-chemical interaction occurred that is independent of the effect of temperature. This is all possible because the self-referencing optical sensor has a lower (reference) waveguide grating structure with a thickness that was sized to make a rate of change of a lower resonant wavelength/temperature variation ($\Delta\lambda^L/\Delta T$) substantially equal to a rate of change of an upper resonant wavelength/temperature variation ($\Delta\lambda^U/\Delta T$). Several other embodiments of self-referencing optical sensors which have a specific structures and/or a specific compositions are also described herein.

32 Claims, 13 Drawing Sheets

U.S. PATENT DOCUMENTS

| | | | |
|---|---|---|---|
| 2003/0027328 A1 | 2/2003 | Cunningham et al. | ... 435/287.2 |
| 2003/0032039 A1 | 2/2003 | Cunningham et al. | ......... 435/6 |
| 2003/0059855 A1 | 3/2003 | Cunningham et al. | ....... 435/7.9 |
| 2003/0068657 A1 | 4/2003 | Lin et al. | ..................... 435/7.9 |
| 2003/0077660 A1 | 4/2003 | Pien et al. | .................. 435/7.1 |
| 2003/0092075 A1 | 5/2003 | Pepper | ...................... 435/7.9 |
| 2003/0113766 A1 | 6/2003 | Pepper et al. | .................. 435/6 |
| 2004/0132172 A1 | 7/2004 | Cunningham et al. | ... 435/287.2 |
| 2004/0132214 A1 | 7/2004 | Lin et al. | .................... 436/518 |
| 2004/0151626 A1* | 8/2004 | Cunningham et al. | ........ 422/58 |
| 2004/0223881 A1 | 11/2004 | Cunningham et al. | ... 422/82.05 |
| 2004/0248318 A1* | 12/2004 | Weinberger et al. | ........ 436/173 |

OTHER PUBLICATIONS

A.Y. Cho, "Observation of Confined Propagation in Bragg Waveguides", Applied Physics Letters, vol., 30, No. 9, May 1, 1977, pp. 471-472.

M.A. Duguay et al., "Antiresonant Reflecting Optical Waveguides in $SiO_2$-Si Multilayer Structures", Applied Physics Letters, vol. 49, No. 1, Jul. 7, 1986, pp. 13-15.

S. Peng et al., "Resonant Scattering from Two-Dimensional Gratings", Journal Optical Society of America A, vol. 13, No. 5, May 1996, pp. 993-1005.

S.S. Wang et al., "Guided-Mode Resonance in Planar Dielectric-Layer Diffraction Gratings", Journal Optical Society of America A, vol. 7, No. 8, Aug. 1990, pp. 1470-1474.

N.J. Goddard et al., "Internally-Referenced Resonant Mirror Devices for Dispersion Compensation in Chemical Sensing and Biosensing Applications", Sensors and Actuators A, vol. 100, 2002, pp. 1-9.

A. Yariv, "Optical Electronics: Propagation, Modulation, and Oscillation in Optical Dielectric Waveguides", 4th Edition, Saunders College Publishing, 1991, pp. 479-487.

\* cited by examiner

SELF-REFERENCING WAVEGUIDE GRATING SENSORS

BACKGROUND OF THE INVENTION

1. Field of the Invention

The present invention relates in general to self-referencing grating-based waveguide sensors (e.g., optical sensors) that are used to detect the occurrence of a bio-chemical interaction (e.g., biological binding of antigen-antibody pairs).

2. Description of Related Art

Grating-based waveguide optical sensors have been used in a wide variety of applications and devices including for example optical filters, laser cavity mirrors and biosensors. In the biosensing application, an optical interrogation system is used to monitor changes in the refractive index or variations in the optical response of the optical sensor as a biological substance is brought into a sensing region of the optical sensor. The presence of the biological substance alters the optical response of the optical sensor when it causes a bio-chemical interaction like material binding, adsorption etc. . . . This alteration of the optical response enables one to use the optical sensor to directly monitor biological events in label-free assays where the expense and experimental perturbations of fluorescent dyes are completely avoided. Unfortunately, in addition to enabling the detection of variations in the optical response due to an bio-chemical interaction, the optical sensor is sensitive to environmental conditions such as temperature, pressure and changes in the bulk refractive index of the buffer solution. The buffer solution is the fluid used to reference the start and end-point of sensing measurements before and after the introduction of the chemical or biological fluid which contains the biological substance that can cause the bio-chemical interaction. As such, there is a need for an optical sensor that is designed to be self-referencing so one can separate the effects of a bio-chemical interaction like a surface binding from changes in environmental conditions. This need and other needs are satisfied by the self-referencing optical sensors and methods of the present invention.

BRIEF DESCRIPTION OF THE INVENTION

The present invention includes self-referencing optical sensors and methods that are used to detect bio-chemical interactions (e.g., biological binding of antigen-antibody pairs) that occur in for example a microplate. In one embodiment, the self-referencing optical sensor includes a substrate, a lower (reference) waveguide grating structure, a buffer layer and an upper (sensing) waveguide grating structure. This self-referencing optical sensor enables an optical interrogation system to detect a bio-chemical interaction independent of the effect of temperature by measuring a reference signal associated with the lower (reference) waveguide grating structure and measuring a sensing signal associated with the upper (sensing) waveguide grating structure. These two signals are then subtracted from one another to determine a sensing measurement that represents whether or not the bio-chemical interaction occurred that is independent of the effect of the temperature. This is all possible because the self-referencing optical sensor has a lower (reference) waveguide grating structure with a thickness that was sized to make a rate of change of a lower resonant wavelength/temperature variation ($\Delta\lambda^L/\Delta T$) substantially equal to a rate of change of an upper resonant wavelength/temperature variation ($\Delta\lambda^U/\Delta T$). Several other embodiments of self-referencing optical sensors which have a specific structures and/or a specific compositions are also described herein.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Figure 1A:
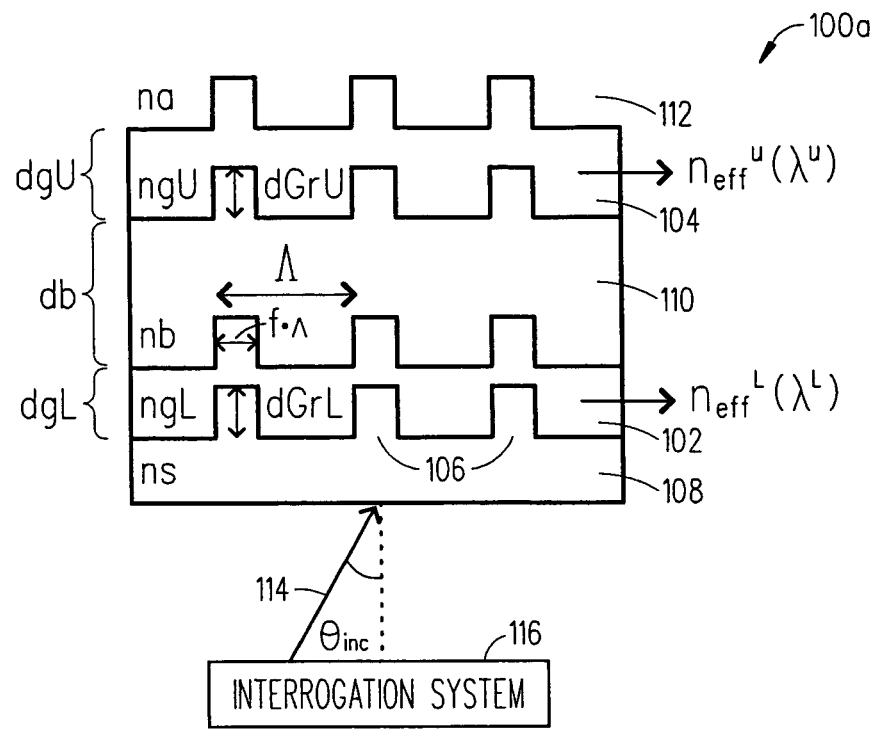
FIGS. 1A–1F are several diagrams associated with a first embodiment of the self-referencing optical sensor in accordance with the present invention.

Referring to FIGS. 1A–1F, there are shown several diagrams associated with a first embodiment of the self-referencing optical sensor $100a$ in accordance with the present invention. As described in greater detail below, the optical sensor $100a$ incorporates two waveguide grating structures 102 and 104 which provide a reference signal and a sensing signal. And, by optimizing the values of the waveguide grating structures 102 and 104, it is possible to athermalise the operation of the optical sensor $100a$. FIG. 1A shows the structure of the optical sensor $100a$. A grating 106 is formed in the substrate 108 (index ns). The substrate 108 is coated with thin films to form the lower waveguide grating structure 102 (index ngL and thickness dgL), the buffer layer 110 (index nb and thickness db) and the upper waveguide grating structure 104 (index ngU and thickness dgU). The film coatings are approximately conformal to the underlying substrate 108. However, the optical sensor $100a$ can also have a different grating depth dGrL and dGrU appearing at the lower and upper waveguide grating structures 102 and 104. The grating period is $\Lambda$ and the duty cycle f. The superstrate medium 112 (index na) is the chemical or biological fluid to be analyzed. In the presence of surface binding, a thin additional higher index layer (not shown) is to be considered between the surface of the upper waveguide grating structure 104 and the superstrate 112. The thickness of the buffer layer 110 is sufficiently large that the lower waveguide grating structure 102 is very insensitive to the effect of surface binding at or near the surface of the upper waveguide grating structure 104.

In the absence of a surface binding, the upper and lower waveguide grating structures 102 and 104 have different resonance wavelengths $\lambda^U$ and $\lambda^L$. These resonant wavelengths $\lambda^U$ and $\lambda^L$ are a function of the parameters of the structure of the optical sensor 100a and are obtained through equation no. 1a for forward coupling to the waveguide mode:

$$n_{inc}\sin\theta_{inc} = n_{eff}^{U,L}(\lambda^{U,L}) - \frac{\lambda^{U,L}}{\Lambda} \quad (1a)$$

for θinc positive being the incidence angle of the optical beam 114 in air from the interrogation system 116 and $neff^U$ and $neff^L$ are the effective indexes of the waveguide mode propagations which depends on the indices and film thicknesses in the optical sensor 100a. A similar situation occurs for reverse coupling with equation no. 1a being replaced by equation no. 1b:

$$n_{inc}\sin\theta_{inc} = -n_{eff}^{U,L}(\lambda^{U,L}) + \frac{\lambda^{U,L}}{\Lambda} \quad (1b)$$

The waveguide grating dispersion is defined in equation no. 1c:

$$D^{U,L} = \frac{dn_{eff}(\lambda^{U,L})}{d\lambda} \quad (1c)$$

For forward coupling, equation no. 1a can be rewritten in the form shown in equation no. 1d:

$$\lambda^{U,L} = \Lambda \cdot (n_{eff}(\lambda^{U,L}) - n_{inc}\sin\theta_{inc}) \quad (1d)$$

Next, consider a variation of temperature ΔT. Using the chain rule of differentiation shown in equation no. 1e:

$$\frac{d\lambda^{U,L}}{dT} = \Lambda \cdot \frac{dn_{eff}(\lambda^{U,L})}{dT} + \frac{d\Lambda}{dT} \cdot (n_{eff}(\lambda^{U,L}) - n_{inc}\sin\theta_{inc}) \quad (1e)$$

It can be seen that $neff^{U,L}$ changes due to changes in material indices and dimensions associated with a temperature change and because of changes in the resonant wavelengths $\lambda^U$ and $\lambda^L$. The effects of these two changes can be separated by using equation no. 1f:

$$\frac{dn_{eff}(\lambda^{U,L})}{dT} = \frac{\partial n_{eff}}{\partial T} + \frac{\partial n_{eff}}{\partial \lambda} \cdot \frac{\partial \lambda}{\partial T} \quad (1f)$$

Substituting equation nos. 1f and 1a into equation no. 1e gives equation no. 1g:

$$\frac{d\lambda^{U,L}}{dT} = \Lambda \cdot \left(\frac{\partial n_{eff}}{\partial T} + D^{U,L} \cdot \frac{d\lambda^{U,L}}{dT}\right) - \frac{d\Lambda}{dT}\frac{\lambda^{U,L}}{\Lambda} \quad (1g)$$

Using the following substitutions in equation no. 1h:

$$a^{U,L} = \frac{\partial n_{eff}}{\partial T} \quad (1h)$$

$$b = \frac{d\Lambda}{dT} = \Lambda \cdot CTE$$

$$x = \frac{d\lambda^{U,L}}{dT}$$

Then equation no. 1g gives equation no. 1i:

$$x = \Lambda \cdot (a^{U,L} + D^{U,L} \cdot x) - b \cdot \frac{\lambda^{U,L}}{\Lambda} \quad (1i)$$

Solving this algebraic equation for x, it can be found that the rate of change of resonant wavelengths $\lambda^U$ and $\lambda^L$ with temperature variation can be represented in equation no. 1j:

$$\frac{\Delta\lambda^{U,L}}{\Delta T} = \frac{\left(a^{U,L} + \frac{b \cdot \lambda^{U,L}}{\Lambda}\right)}{(1/\Lambda - D^{U,L})} \quad (1j)$$

This equation also holds true for a reverse coupling of the incident beam 114 to the waveguide mode.

Figure 1B:
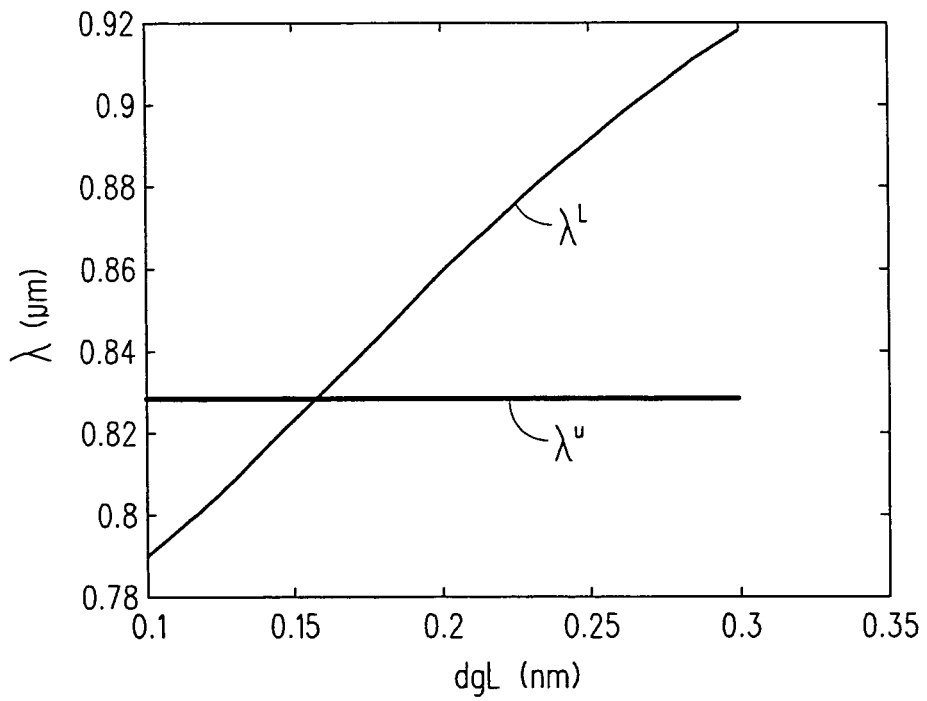

FIG. 1B is a graph that shows the resonance wavelengths $\lambda^U$ and $\lambda^L$ in the absence of surface binding for the upper and lower waveguide grating structures 104 and 102 as the lower waveguide thickness dgL is varied. As can be seen, the resonance wavelength $\lambda^U$ remains constant while the resonance wavelength $\lambda^L$ varies as the lower waveguide thickness dgL is varied. The example parameters used to generate this graph were ngU=ngL=2.1, nb=1.45, dgU=190 nm, db=550 nm, na=1.333, ns=1.51, Λ=500 nm, incident beam angle $\theta_{inc}$ in air was 1.7° and polarization TM.

Figure 1C:
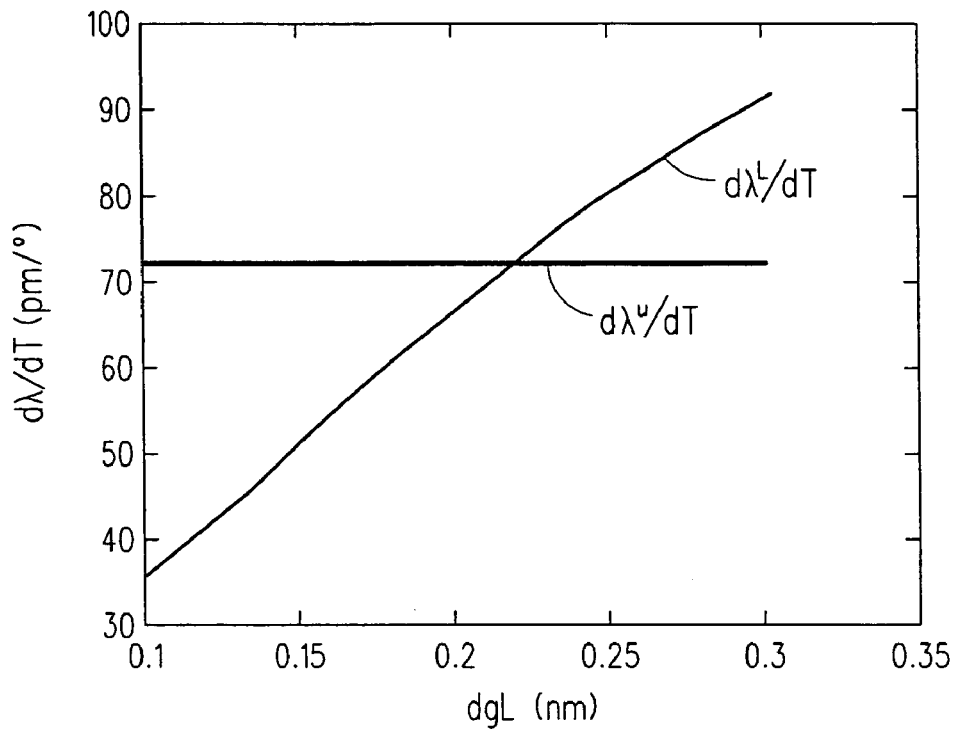

Since an aim in this embodiment of the present invention is to athermalise the operation of the self-referenced waveguide grating sensor 100a, one needs to consider the variation of the structure parameters with temperature. For simplicity, assume that the total temperature variation of all of the layers in the optical sensor 100a can be modeled through a refractive index variation with temperature of the lower and upper waveguide grating structures 102 and 104 and a thermal expansion of the grating period Λ. In one example, the material dn/dT coefficients of $1.2e^{-4}$ and $1.0e^{-4}$ were used for the upper and lower waveguide grating structures 102 and 104, respectively. This allowed the recalculation of the neff and hence $a^{U,L}$ for a small temperature variation. The coefficient of thermal expansion $b=3e^{-5}$ was used for the grating pitch Λ. FIG. 1C is a graph that shows the result of this calculation of the rate of change of resonance wavelengths for variations of temperature for the lower and upper waveguide grating structures 102 and 104. As can be seen, the variation of $d\lambda^L/dT$ for the lower waveguide grating structure 102 was a function of its thickness. And, $d\lambda^U/dT$ remained constant as the thickness varied in the lower waveguide grating structure 102.

As can also be seen in FIG. 1C there is an optimal value of the thickness of the lower waveguide grating structure 102 for which $d\lambda^L/dT$ and $d\lambda^U/dT$ are equal for both the lower and upper waveguide grating structures 102 and 104. In this situation, the optical sensor 100a is athermalised where changes of temperature affect equally the upper and lower waveguide grating resonance wavelengths. Therefore, by using the difference between the upper and lower resonance wavelengths the sensing measurement is independent of the effect of temperature. The optimal thickness dgL of the lower waveguide grating structure 102 in this example was 218.8 nm.

It should be appreciated that the optical sensor 100a can be used in a way to obtain resonant wavelength insensitivity to angle misalignment of the optical beam 114 from the interrogation system 116. Equation no. 1a implies that resonant wavelengths $\lambda^U$ and $\lambda^L$ are sensitive to the alignment angle $\theta_{inc}$ (typically ~7 nm/°) of the optical beam 114. Therefore, to have a highly sensitive wavelength detection system (resolution ~0.1 pm) one also needs to be able to reference out the sensitivity of the incidence angle $\theta_{inc}$ of the interrogation beam 114. There are a number of different ways of doing this including for example: (1) using the waveguide grating resonance properties of forward and reverse propagation; (2) using the waveguide grating resonance properties when reversing input and output beams; or using an optical deflection system for local surface angle measurement.

Figure 1D:
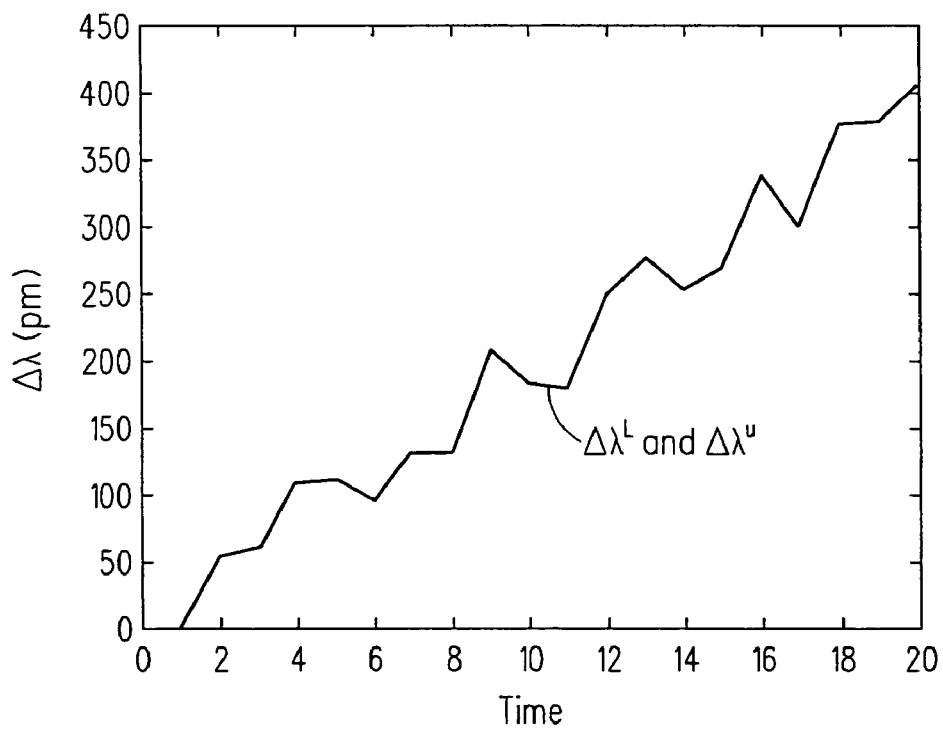
Figure 1E:
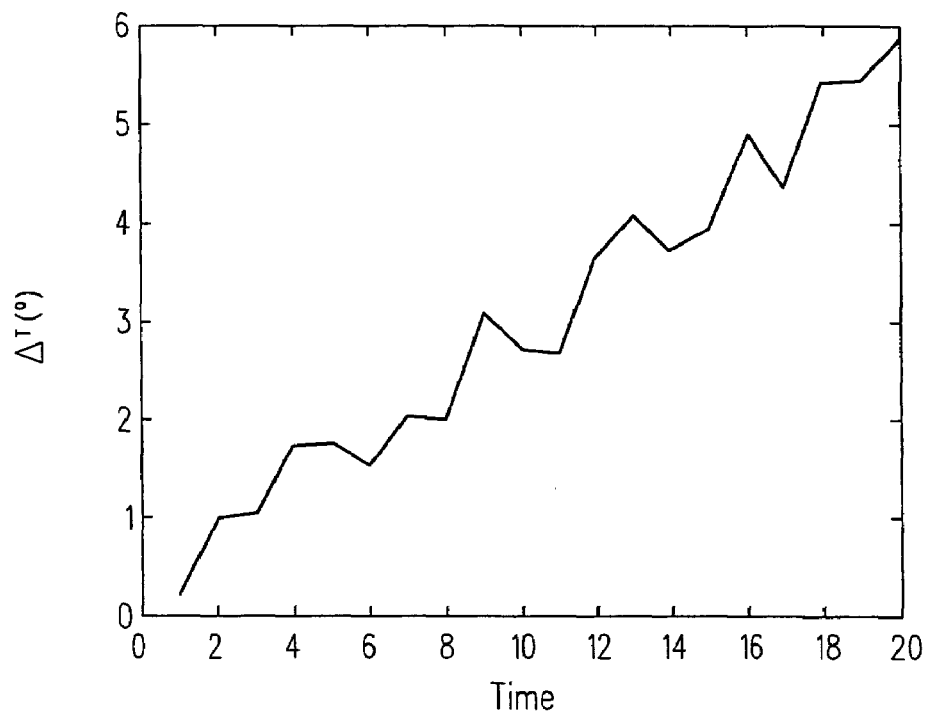
Figure 1F:
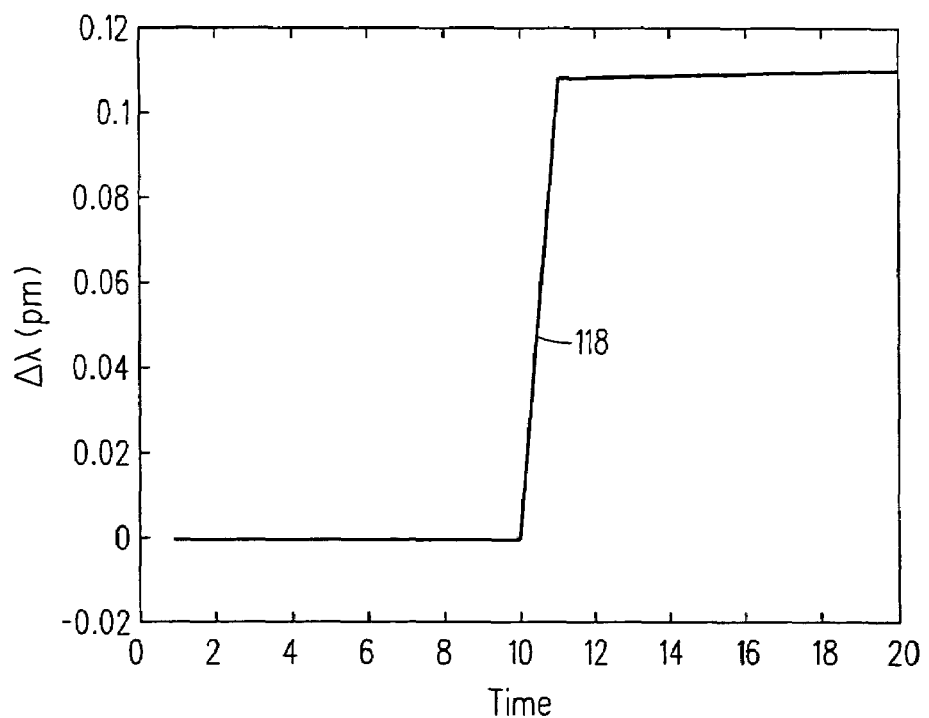

FIGS. 1D–1F are three graphs that were generated during a simulated variation in the optical sensor 100a where the sensor wavelengths $\lambda^U$ and $\lambda^L$ (see FIG. 1D) changed due to a temperature variation of roughly 6° C. (see FIG. 1E). It should be noted that the wavelength variation of roughly 400 pm due to temperature completely masked that due to an index change (0.1 pm). However, in the case that the $d\lambda/dT$ for both the lower and upper waveguide grating structures 102 and 104 were well matched, the difference signal 118 can be readily seen between the two waveguide grating wavelengths $\lambda^U$ and $\lambda^L$ (see FIG. 1F).

From the foregoing, it can be readily appreciated by those skilled in the art that the present embodiment enables the use of spectral interrogation to detect bulk or surface index changes using the optical sensor 100a by providing a feasible means of referencing out the temperature variations that lead to spurious wavelength variations. In addition, the present invention is simpler to implement than the device disclosed in U.S. Pat. No. 6,455,004 B1 which provides temperature referencing for an angular interrogation scheme but is complicated by the use of multiple separate grating pads operating in different polarization. Moreover, the present invention surpasses the referencing scheme disclosed in the article by Goddard et al. entitled "Internally-Referenced Resonant Mirror Devices for Dispersion Compensation in Chemical Sensing in Biosensing Applications" Sensors and Actuators A 100 (2002). Because, it uses an additional waveguide layer to reference temperature together with an external angle/wavelength reference rather than using the additional waveguide layer to reference angle/wavelength variations without compensating for temperature. The contents of both of these documents are incorporated by reference herein.

Referring to FIGS. 2A–2F, there are shown several diagrams associated with a second embodiment of the self-referencing optical sensor 100b in accordance with the present invention. As described above, the first embodiment of the optical sensor 100a is based on the use of two waveguide grating structures 102 and 104 each of which have resonances $\lambda^U$ and $\lambda^L$ that can be interrogated independently. In particular, the upper waveguide grating structure 104 is optimized for high sensitivity to biological binding at its surface. And, the lower waveguide grating structure 102 is separated from the upper waveguide grating structure 104 and the binding surface by a buffer layer 110 so that it can be very insensitive to binding. In addition, it was shown that the structure of the optical sensor 100a can be optimized for athermal operation where the resonance wavelengths $\lambda^U$ and $\lambda^L$ of each waveguide grating structure 102 and 104 change by the same amount for a thermal fluctuation on the system. The difference between the two wavelengths $\lambda^U$ and $\lambda^L$ is then representative of a surface binding event independent of thermal variations. Although the optical sensor 100a works well the fabrication of it requires the deposition of three index layers 102, 104 and 110 with very precisely controlled indices and thicknesses. It is one purpose of the second embodiment of the present invention to propose an equivalent functional optical sensor 100b that is based on different physical phenomena and offers a simplified fabrication process when compared to optical sensor 100a.

Figure 2A:
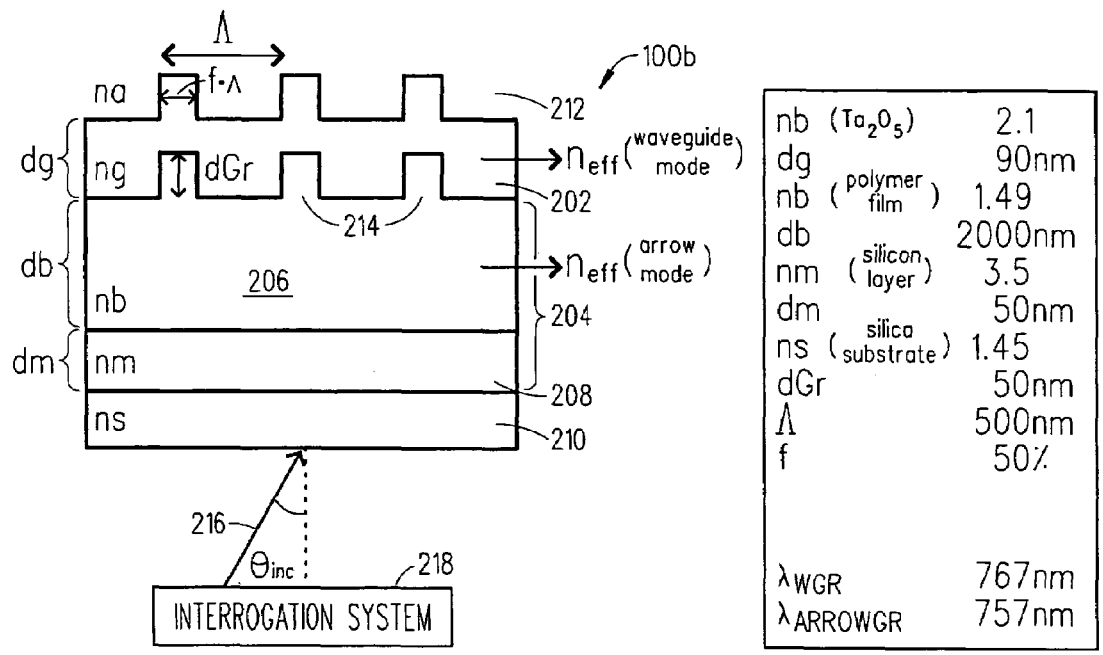
FIGS. 2A–2F are several diagrams associated with a second embodiment of the self-referencing optical sensor in accordance with the present invention.
Figure 2B:
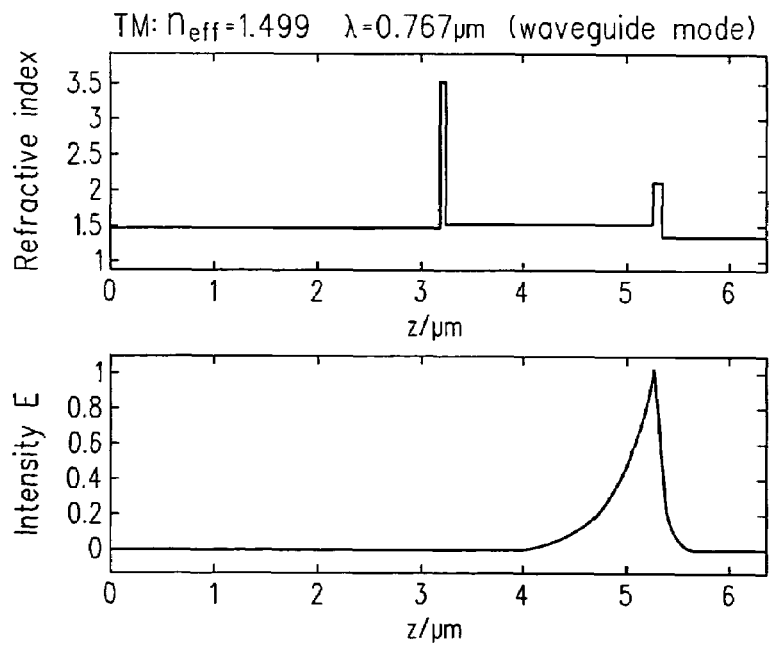
Figure 2C:
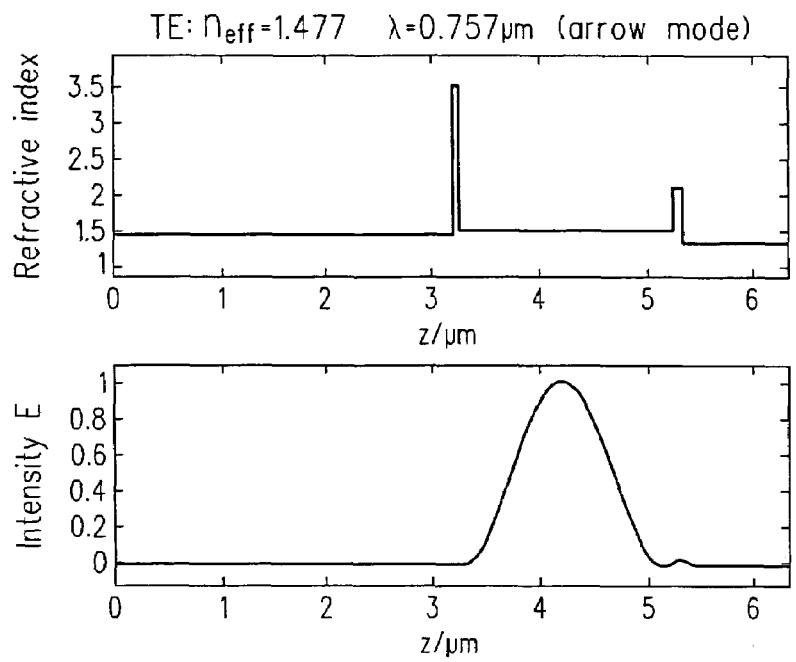

The optical sensor 100b incorporates a waveguide grating structure 202 together with an anti-resonant reflecting optical waveguide (ARROW) grating structure 204 in order to provide a sensing signal and a reference signal, respectively. FIG. 2A shows the structure of the optical sensor 100b with the ARROW grating structure 204 and exemplary parameters and materials of construction. The waveguide grating structure 202 is formed by a cast and cure process on a buffer/polymer layer 206 (nb). Prior to this, however, a thin and high index layer 208 (nm) is deposited on a substrate 210 (ns). It is this layer 208 that acts as a high reflectivity mirror for light so it is confined in the buffer/polymer layer 206. In fact, this layer 208 acts as a Fabry Perot cavity. The thin layer 208 transmits a narrow band of wavelengths on resonance and reflects a broad band off resonance. In the example shown in FIG. 2A, the film 208 has a thickness of 50 nm and index 3.5 so the first resonance wavelength is at 350 nm, roughly half the mode wavelength so it can be used as a reflector. Because, the waveguide confinement occurs due to this anti-resonant reflection on the substrate side (there is no index confinement at the substrate interface), then this mode is termed ARROW mode. The reflection from such a thin layer 208 is efficient because the ARROW mode is striking it at grazing incidence. It is also insensitive to the precise wavelength of operation since the anti-resonance behavior occurs over a broad wavelength band.

Now, despite the ARROW mode being localized in the immediate vicinity of the waveguide grating structure 202, it is relatively insensitive to surface binding. For the exemplary optical sensor 100b, the waveguide mode effective index is 47× more sensitive to surface binding than the ARROW mode effective index. The calculation of surface binding sensitivity can be made from equation no. 2a:

$$F_s = \frac{\Delta n_{\text{eff}}}{\Delta t_{\text{bio}}} \quad (2a)$$

where neff is calculated for a uniform index=1.333 analyte layer 212 (na) and then neff is calculated for a 5 nm film (not shown) of index 1.5 on the surface of the waveguide grating structure 202. The neff for the waveguide mode and ARROW mode are different and respond differently to the surface binding film (see FIGS. 2B and 2C). This calculation shows that the waveguide mode has a change of neff 47× when compared to the ARROW mode for the same binding layer.

Figure 2D:
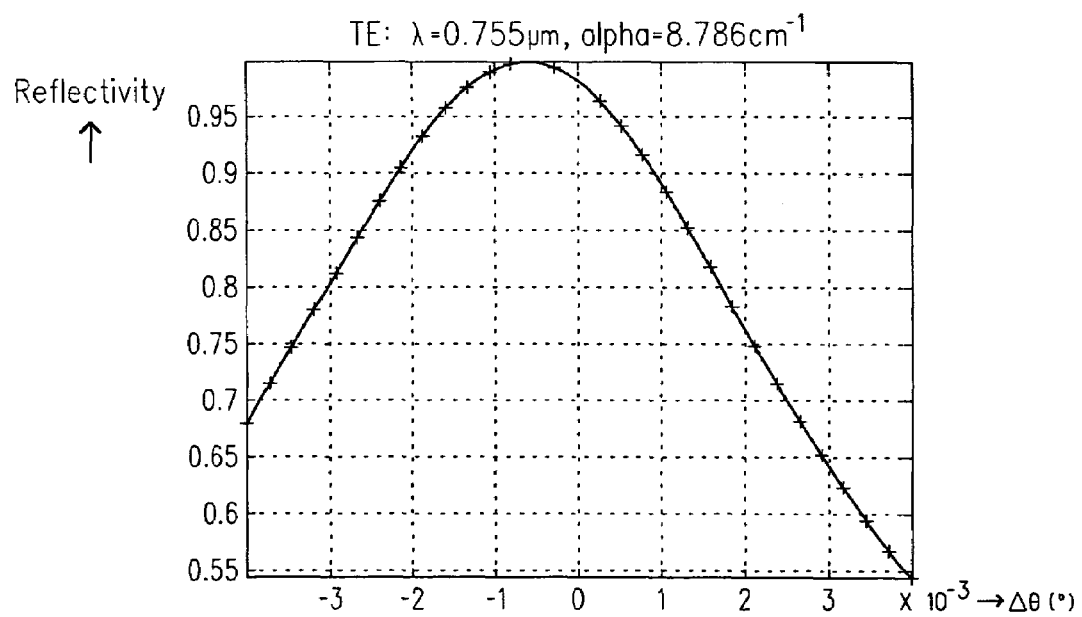
Figure 2E:
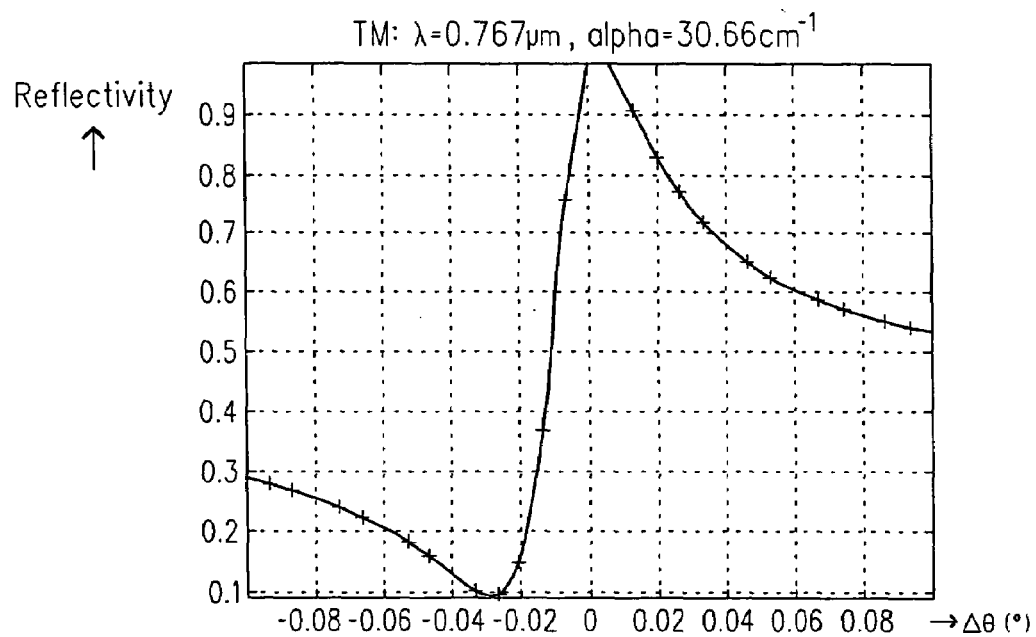
Figure 2F:
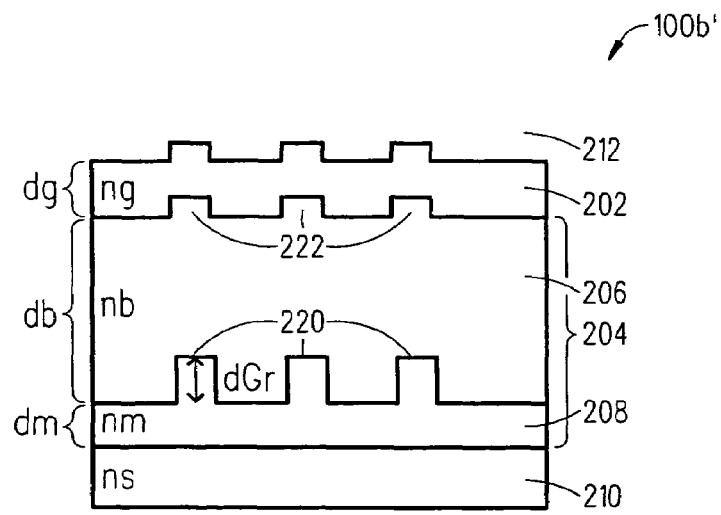

In the above design, the waveguide mode operates in TM polarization while the ARROW mode in TE polarization. In fact, the ARROW mode is extremely lossy in TM polarization because the reflection efficiency of the thin, high index layer 208 is much lower for this polarization at grazing incidence. When the ARROW mode is excited by a wave incident on the grating 214, then the grating coupling coefficient, or leakage, is $\alpha=8.8$ cm$^{-1}$ as shown in FIG. 2D from rigorous coupled wave analysis (RCWA) and resonant excitation analysis. To achieve a comparable coupling coefficient for the same grating depth dGr, the waveguide grating resonance needs to operate in TM polarization because $\alpha$ for TE would be much higher and therefore it would be difficult to efficiently excite both modes with the same beam 216 emitted from an interrogation system 218. FIG. 2E shows the RCWA calculation for the waveguide grating resonance reflection having $\alpha=30.7$ cm$^{-1}$. An alternative way to address this "$\alpha$ matching" problem would be to use the optical sensor 100b' shown in FIG. 2F which has different grating depths for the ARROW and sensing waveguide layers 202 and 204. The exemplary optical sensor 100b' shown has a deep (>50 nm) grating layer 220 that can be formed under the buffer/polymer layer 206. When covered with the thick buffer/polymer layer 206, the grating 220 can be smoothed out so that a much shallower grating 222 is in the vicinity of the sensing waveguide layer 202. In an alternative embodiment, the buffer layer 206 need not be a polymer if the grating layer 220 is formed in the reflector layer nm. This grating layer 220 could be formed by etching or by having the embossable polymer under the reflector layer nm.

It should be appreciated that alpha represents the leakage rate of the resonant sensor 100b and 100b'. It governs both the linewidth of the resonance and also the reflection efficiency. When there are two resonances as in the case of the waveguide grating+ARROW layer, then one would like to have similar linewidth and excitation efficiency to simplify the signal treatment. This is what is call herein as "alpha matching". The problem is that for the ARROW layer 204 and waveguide grating structure 202, the alpha is inherently different due to the different physics so as described above one layer is operated in TE polarization and the other layer is operated in TM polarization or different grating depths are used to bring the alphas closer together.

Figure 3:
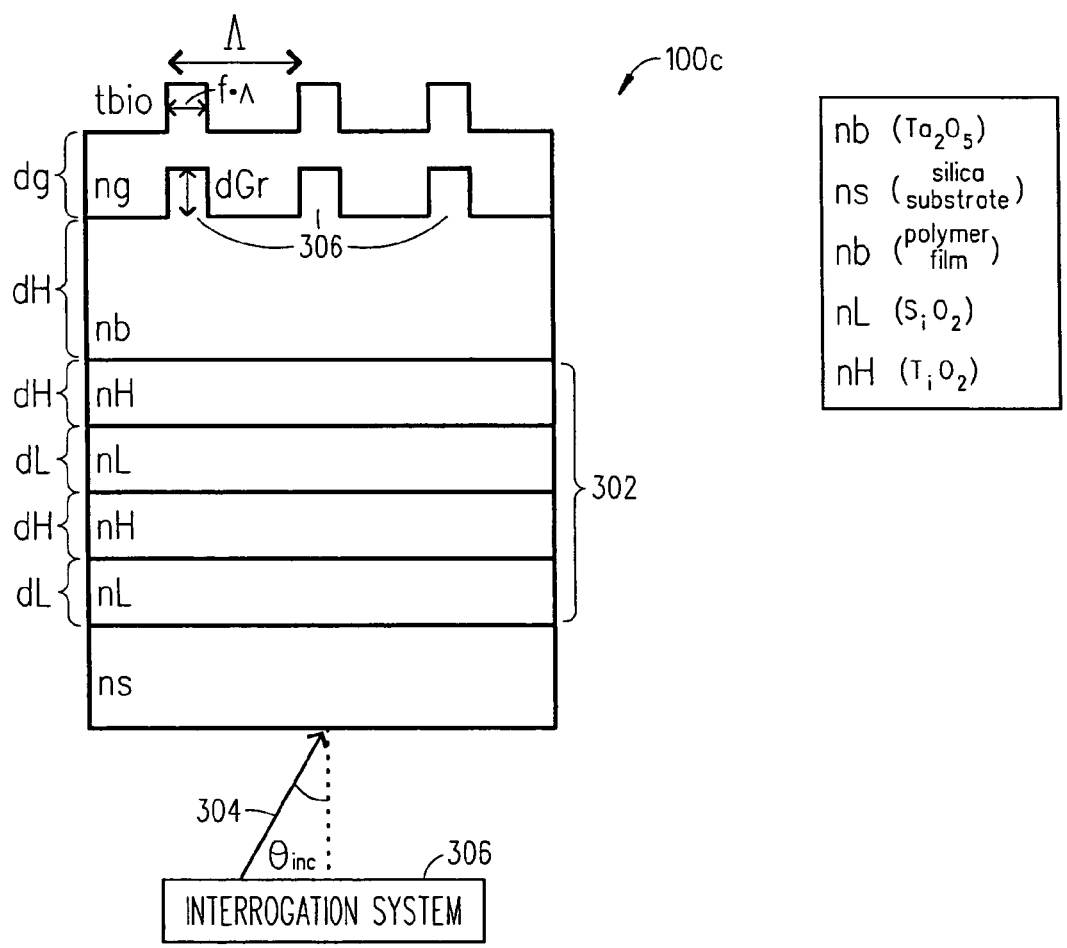
FIG. 3 is a diagram associated with a third embodiment of the self-referencing optical sensor in accordance with the present invention.

Referring to FIG. 3, there is a diagram associated with a third embodiment of the self-referencing optical sensor 100c in accordance with the present invention. In this embodiment, the optical sensor 100c instead uses a Bragg mirror 302 for mode confinement shown as plurality of dielectric mirrors nL and nH instead of using an ARROW structure and still can achieve the same waveguiding in the buffer/polymer layer nb. FIG. 3 shows the structure of the waveguide grating sensor 100c with a reference waveguide formed with a Bragg mirror 302 that is being interrogated by an optical beam 304 emitted from an interrogation system 306.

Using optimized values of the indices and layer thickness in the structure, and possibly additional index layers, it is possible to athermalise the operation of the optical sensor 100c using a similar technique as was done to design optical sensor 100a (see FIGS. 1A–1F). That is, to ensure that the wavelength shift with temperature is the same for both the sensor and reference signals. A particular neff for a resonance leads to a precise resonance wavelength $\lambda$. This wavelength changes with temperature because the material index changes with temperature. The $d\lambda/dT$ for the waveguide grating resonance and the BRAGG resonance will, in general, be different. However, by adjusting the material indices and thicknesses it is possible to find situations in which the $d\lambda/dT$ for the two resonances match, as was shown above with respect to the optical sensor 100a (see FIGS. 1A–1F).

Alternatively, an approach which eases the fabrication tolerances on the optical sensor 100c is to implement a temperature compensation scheme. In this scheme, the thermal coefficients $K_S$ and $K_R$ for the sensor and reference wavelengths $\lambda_S$ and $\lambda_R$ are defined by equation no. 3a:

$$K_S = \frac{d\lambda_S}{dT} \tag{3a}$$

$$K_R = \frac{d\lambda_R}{dT}$$

And, wavelength interrogation slopes due to the surface binding of a thin biolayer, $t_{bio}$, for sensor and reference are defined by equation no. 3b:

$$C_S = \frac{d\lambda_S}{dt_{bio}} \tag{3b}$$

$$C_R = \frac{d\lambda_R}{dt_{bio}}$$

Then the real change of sensor and reference wavelengths $\lambda_S$ and $\lambda_R$ are given by equation no. 3c:

$$\lambda_S = C_S \cdot \Delta t_{bio} + K_S \cdot \Delta T$$

$$\lambda_R = C_R \cdot \Delta t_{bio} + K_R \cdot \Delta T \tag{3c}$$

By resolving this pair of linear equations one can separate the surface binding effect from the temperature change.

To obtain the actual surface thickness or bulk index change, the above equations can be written in matrix form and then inverted:

$$\begin{pmatrix} \lambda_S \\ \lambda_R \end{pmatrix} = M \begin{pmatrix} \Delta t_{bio} \\ \Delta T \end{pmatrix} \tag{3d}$$

$$M = \begin{pmatrix} C_S & K_S \\ C_R & K_R \end{pmatrix}$$

where $$\begin{pmatrix} \Delta t_{bio} \\ \Delta T \end{pmatrix} = M^{-1} \begin{pmatrix} \lambda_S \\ \lambda_R \end{pmatrix}$$

From the foregoing, it can be readily appreciated by those skilled in the art that the optical sensors 100b and 100c (see FIGS. 2–3) can be fabricated more easily than optical sensor 100a (see FIGS. 1A–1F). The UV polymer/buffer material nb in which the grating 214 or 306 is formed is itself used as a reference waveguide, operating by ARROW or Bragg confinement. Therefore, no second high index waveguide deposition is needed. Further, in the ARROW optical sensor 100b, the thickness of the thin, high index layer dm is not a critical, low tolerance, parameter due its anti-resonance operation.

Figure 4A:
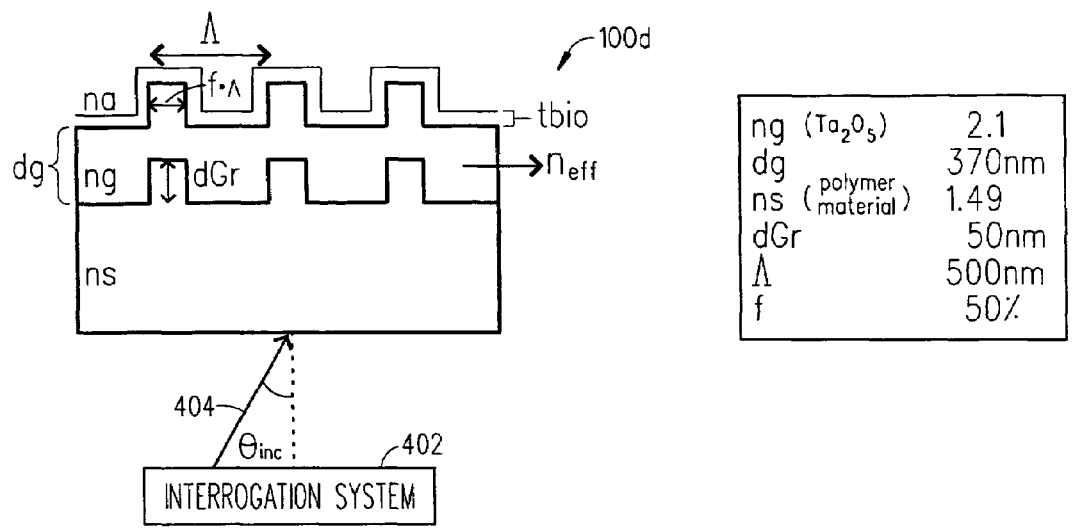
FIGS. 4A–4C are several diagrams associated with a fourth embodiment of the self-referencing optical sensor in accordance with the present invention.
Figure 4B:
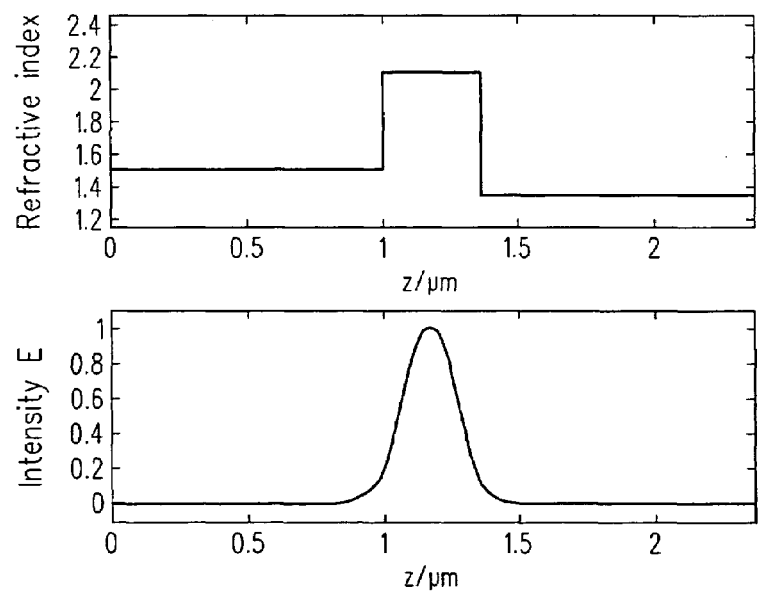
Figure 4C:
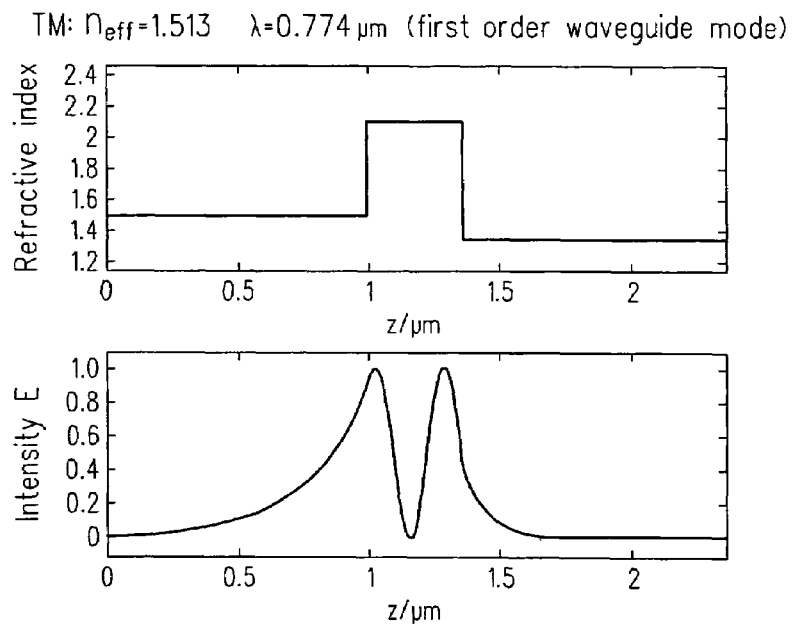

Referring to FIGS. 4A–4C, there are shown several diagrams associated with a fourth embodiment of the self-referencing optical sensor 100d in accordance with the present invention. In this embodiment, the higher order mode properties of the optical sensor 100d are used to separate the effects of surface binding from bulk index changes. As described in greater detail below, the optical sensor 100d can have different resonances corresponding to the different propagating modes of the waveguide. And, the field profiles of the different modes are unique and therefore lead to different bulk and surface sensitivities of the different modes.

The bulk optical field sensitivity (OFS) is defined through equation no. 4a:

$$F_B = \frac{\Delta n_{eff}}{\Delta n_{analyte}} \quad (4a)$$

where $n_{eff}$ is the waveguide effective index and $n_{analyte}$ is the cover layer index. Similarly, the surface OFS is defined through equation no. 4b:

$$F_S = \frac{\Delta n_{eff}}{\Delta t_{bio}} \quad (4b)$$

where $t_{bio}$ is the biological binding layer thickness.

In a spectral interrogation system 402, the resonance wavelength is related to the effective index (neff), the wavelength ($\lambda$), the grating pitch ($\Lambda$) and the angle of incidence ($\theta_{inc}$) in air of the optical beam 404, through equation no. 1b for reverse coupling.

For instance, consider the exemplary waveguide grating structure 100d having the indices and waveguide thickness listed in FIG. 4A. For a reverse coupling angle of 1.9°, one can find resonance wavelengths of 942 nm and 774 nm for the fundamental (m=0) and first order (m=1) mode coupling of this structure. The corresponding intensity field profiles are shown in FIGS. 4B and 4C.

Now if the bulk and surface OFS are calculated for these two modes one would find the following values shown in TABLE #1:

TABLE #1

|  | m = 0 | m = 1 |
| --- | --- | --- |
| Surface OFS ($\mu m^{-1}$) | 0.241 | 0.283 |
| Bulk OFS ($RIU^{-1}$) | 0.095 | 0.169 |

It can be see that the surface OFS of the two modes are substantially the same but the bulk OFS for the two modes are different. Therefore, when one makes a measurement in a biological or chemical experiment where the measurement signal is either wavelength or angle but the fundamental waveguide property that is modified is the effective index, then the signal changes due to surface binding thickness and bulk index changes. If the measurement is made with both the m=0 and m=1 modes, then variations of surface binding thickness over the course of the test lead to roughly the same signal change for both m=0 and m=1 modes while changes of the bulk index lead to a relative difference between the signals. Therefore, it is possible from the relative change between m=0 and m=1 signals to quantify the amount of surface thickness or bulk index change.

More precisely, the amount of bulk index change $\Delta n_{analyte}$ and surface binding thickness $\Delta t_{bio}$ can be obtained from the resolution of the following pair of linear equations:

$$\Delta n_{eff}^{m=0} = B_0 \cdot \Delta n_{analyte} + S_0 \cdot \Delta t_{bio}$$

$$\Delta n_{eff}^{m=1} = B_1 \cdot \Delta n_{analyte} + S_1 \cdot \Delta t_{bio} \quad (4d)$$

where $B_0$, $S_0$, $B_1$, $S_1$ are the bulk and surface OFS for the two modes. To obtain the actual surface thickness or bulk index change, the above equations can be written in matrix form and then inverted:

$$\begin{pmatrix} \Delta n_{eff}^{m=0} \\ \Delta n_{eff}^{m=1} \end{pmatrix} = M \begin{pmatrix} \Delta n_{analyte} \\ \Delta t_{bio} \end{pmatrix}$$

$$M = \begin{pmatrix} B_0 & S_0 \\ B_1 & S_1 \end{pmatrix}$$

where $$\begin{pmatrix} \Delta n_{analyte} \\ \Delta t_{bio} \end{pmatrix} = M^{-1} \begin{pmatrix} \Delta n_{eff}^{m=0} \\ \Delta n_{eff}^{m=1} \end{pmatrix}$$

From the foregoing, it can be readily appreciated by those skilled in the art that the optical sensor 100d in this embodiment resolves the uncertainty of measurement due to variations of buffer solution refractive index. For a more detailed discussion about the higher mode properties of a waveguide grating resonance (WGR) sensor like the one used in the present embodiment reference is made to the book by A. Yariv entitled "Optical Electronics" 4th Ed., Saunders College Publishing, chapter 13, 1991. The contents of this book which describe general waveguide mode properties and not WGR devices or sensors are incorporated by reference herein.

Referring to FIGS. 5A–5G, there are shown several diagrams associated with a fifth embodiment of the self-referencing optical sensor 100e in accordance with the present invention. The optical sensor 100e described below is suitable for use in bio-chemical assay applications by providing a local wavelength reference that can be used to eliminate the deleterious effects of environmental drifts such as thermal and mechanical variations while simultaneously increasing the bulk and surface sensitivity of the sensor. In fact, the optical sensor 100e has a relatively simple structure since it utilizes only a single replicated grating structure 502 in the substrate 504 and only requires the deposition of three dielectric layers 506, 508 and 510.

Figure 5A:
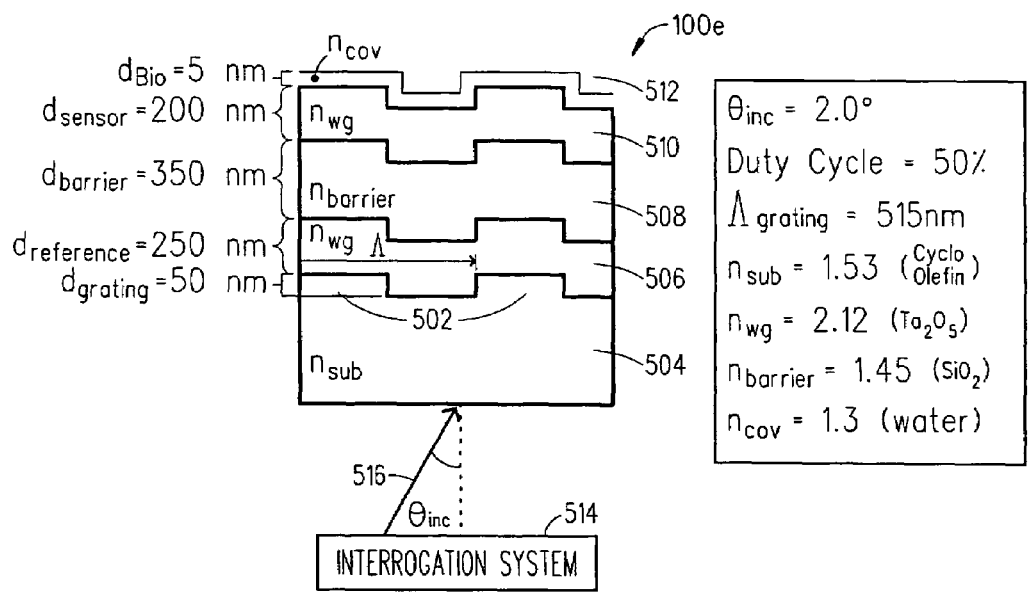
FIGS. 5A–5G are several diagrams associated with a fifth embodiment of the self-referencing optical sensor in accordance with the present invention.

FIG. 5A shows a schematic diagram of an exemplary triple-layer waveguide resonance grating sensor 100e. As can be seen, the optical sensor 100e includes three dielectric layers 506, 508 and 510 deposited over a grating 502 formed in a substrate 504. The various types of materials that can be used to make the substrate 504 include glass, plastic (topaz (cyclo olefin), polycarbonate, etc. . . ), and cured epoxies. In the exemplary optical sensor 100e, $Ta_2O_5$ is used to form the reference and sensing waveguides 506 and 510 and $SiO_2$ is used to form the low-index barrier 508. It is important to note that both waveguides 506 and 510 use the grating pitch $\Lambda$ and depth $d_{grating}$ as defined by the grating 502 that is replicated in the substrate 504. Resonance positions for the two waveguides 506 and 510 are determined by controlling the individual waveguide refractive index and thickness. Other dielectric materials such as $TiO_2$, $Nb_2O_5$, $MgF_2$, etc., and semiconducting materials such as Si, InP, GaAs, etc. can be used in various combinations to optimize the design and performance of the sensor/reference structures 506 and 510. The low-index barrier 508 provides isolation between the reference waveguide 506 and the sensing waveguide 510 such that the reference waveguide 506 is insensitive to changes in the bulk solution 512 and in the cover solution which is located near the target layer surface $d_{Bio}$.

In operation, an interrogation system 514 emits an optical beam 516 so as to interrogate the optical sensor 100e where the reference waveguide 506 senses environmental variations such as thermal and mechanical drift. And, the sensing waveguide 510 senses changes in the refractive index of the cover solution at the target layer surface $d_{Bio}$, changes of the cover solution refractive index in the bulk fluid 512, and the same environmental variations sensed by the reference waveguide 506. As a result, contributions from environmental variations can be subtracted out of the measured response from the sensing waveguide 510 thus leaving only the measurement of surface and bulk fluid refractive index changes. In this discussion, it is assumed that the optical sensor 100e is being operated in the spectral interrogation mode however an angular mode is also possible.

Figure 5B:
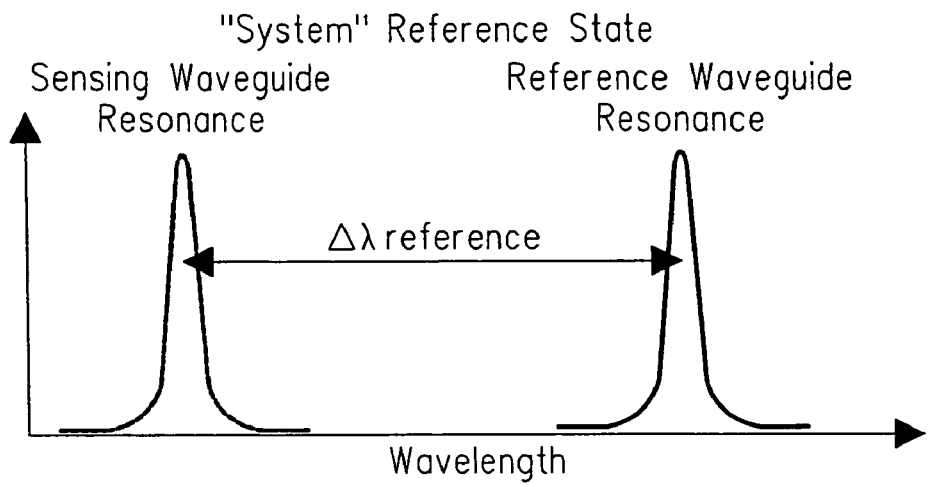
Figure 5C:
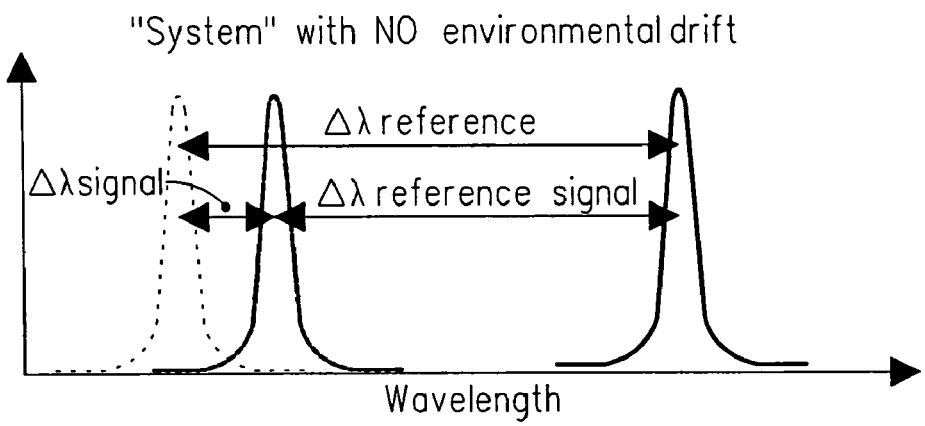
Figure 5D:
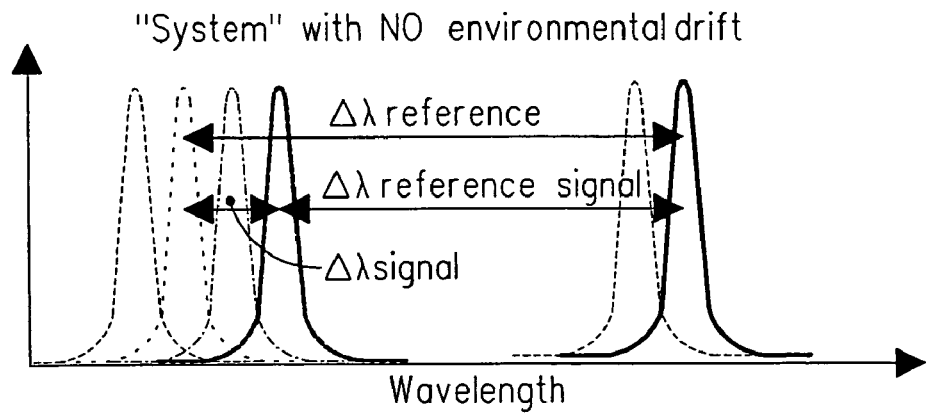

FIGS. 5B–5D are graphs that illustrate the observed $0^{th}$ order reflected diffraction spectra from the triple-layer waveguide grating resonance (WGR) optical sensor 100e. In particular, FIG. 5B illustrates the reference state of the optical sensor 100e, i.e. no bio-chemical substance present. It should be noted that the reference state can be measured with or without environmental drift since the reference state relies on the measurement of the wavelength difference between the resonances $\lambda$ of the reference and sensor waveguides 506 and 510. When a bio-chemical substance is present, i.e. when the refractive index near the sensor surface changes by either properties varying in the bulk solution 512 or by compound molecules binding at the target surface layer $d_{Bio}$ or both, the difference between the resonance of the reference waveguide 506 and the resonance of the sensing waveguide 510 is illustrated in FIG. 5C. Hence, a referenced signal is produced by again measuring the difference between the resonances of the reference waveguide 506 and sensor waveguide 510 and then comparing this difference with the difference obtained in the reference state illustrated in FIG. 5B. When environmental perturbations are present, the reference resonance acts as a local reference that shifts in response with the sensor resonance allowing a referenced measurement to be made as shown in FIG. 5D. In this way, the optical sensor 100e enables the separation of environmentally induced resonance shifts from resonance shifts of interest induced by property changes in the bulk solution 510 and by binding of drug compounds at the target surface layer $d_{Bio}$.

For optimum performance of the optical sensor 100e, the reference resonance should be insensitive to changes in the bulk and surface regions above the sensing waveguide 510. To accomplish this, the optical sensor 100e needs to be designed properly. One such, properly designed optical sensor 100e with waveguide and barrier refractive indices and thicknesses is shown in FIG. 5A. For proper operation of the reference waveguide 506, the thickness and refractive index of the barrier 508 need to be chosen to provide high isolation for the reference waveguide quasi-guided modes. These modes are referred to as modes quasi-guided since they are lossy modes due to the presence of the grating 502 and hence are not true bound modes of the waveguide 506. It should be noted that the terms guided mode and quasi-guided mode are used interchangeably herein. The barrier 508 also provides increased sensitivity by biasing the quasi-guided mode for the sensing waveguide 510 towards the bulk solution 512 and the target layer surface $d_{Bio}$. The parameters detailed in FIG. 5A represent one possible implementation of the optical sensor 100e.

Figure 5E:
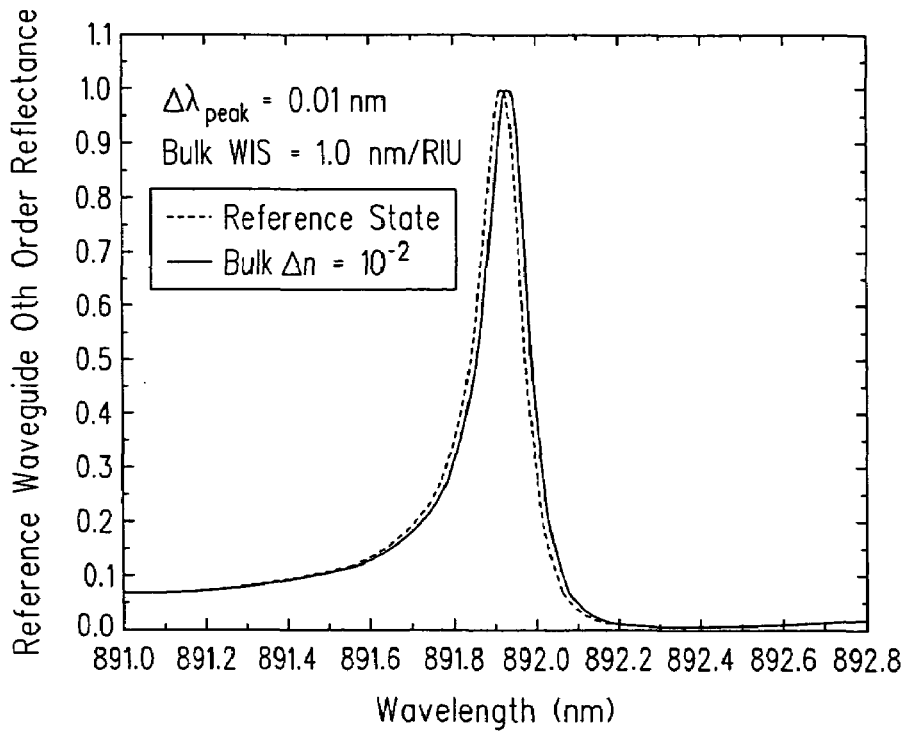
Figure 5F:
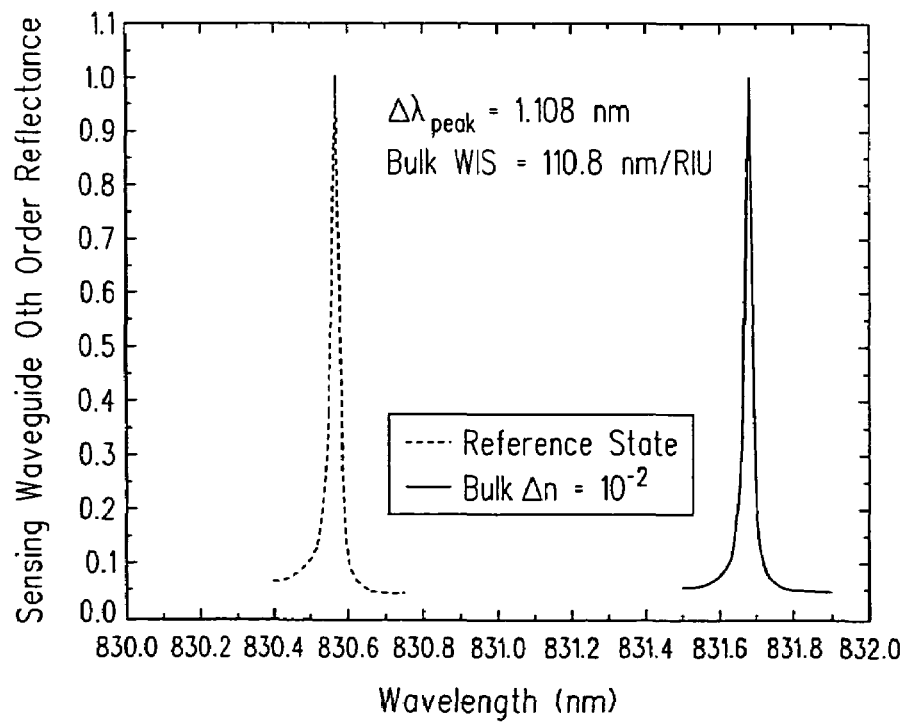
Figure 5G:
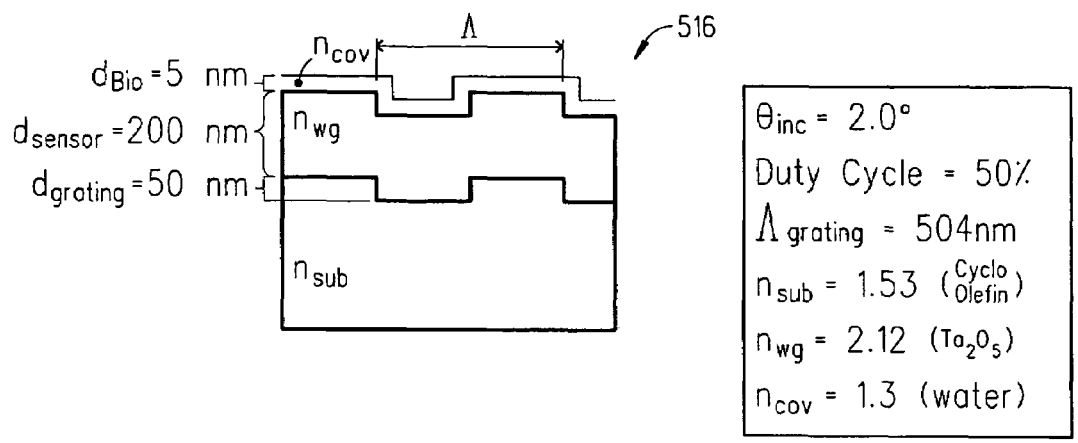

The exemplary optical sensor 100e shown in FIG. 5A was analyzed by using Rigorous Coupled Wave Analysis (RCWA) and the results are shown in FIGS. 5E–5F. The results shown in the graphs of FIGS. 5E–5F were calculated assuming a TM polarized incident field and assuming only bulk refractive index changes were present. Similar results would be obtained if surface refractive index changes were assumed to be present and/or the TE waveguide resonance was utilized. As shown in FIG. 5F, the sensing waveguide sensitivity to a $1 \times 10^{-2}$ bulk refractive index change was found to be 1.108 nm, resulting in a bulk Wavelength Interrogation Slope (WIS) of 110.8 nm per Refractive Index Unit (RIU) of change or 110.8 nm/RIU. For the design of the barrier 508 considered in FIG. 5A, the resulting bulk WIS of the reference waveguide for the same bulk refractive index change was only 0.01 nm or a bulk WIS of 1.0 nm/RIU as found in FIG. 5E. The result is an isolation factor of approximately 111 or 20.5 dB between the reference and sensing waveguides 506 and 510.

An additional benefit of the optical sensor 100e is that the low refractive index barrier 508 which provides isolation for the reference waveguide 506 also simultaneously increases the sensitivity of the sensing waveguide 510. To quantify the increased sensitivity, the optical sensor 100e is compared to a traditional single dielectric layer sensor 516 (see FIG. 5G). Assume the same materials are used with the same refractive indices. And, the only design change made to the structure is a change in the grating pitch $\Lambda$ to accommodate the change in the refractive index of the substrate. Using RCWA, the bulk WIS of the traditional sensor 516 was found to be 92.4 nm/RIU. The resulting WIS improvement obtained with the exemplary optical sensor 100e is 20% over the traditional single-layer optical sensor 516.

As can be seen, the optical sensor 100e produces a very stable reference resonance that provides each sensor in a biochemical assay application with a local absolute wavelength sensor that is sensitive only to environmental perturbations and simultaneously increases the sensor sensitivity. The end result, is an increased sensitivity, self-referenced sensor design that allows the detection of bulk and surface layer refractive index changes by monitoring the relative spectral shift between the resonances of the reference waveguide 506 and the sensing waveguide 510. Finally, different material combinations, such as Si and $SiO_2$, can be used to increase the isolation and sensitivity beyond the values described above.

For a more detailed discussion about the operating principle of the sensor 100e in terms of resonance wavelength and sensitivity then reference is made to the following technical literature:

- S. S. Wang, et al. "Guided-mode resonances in planar dielectric-layer diffraction gratings," J. Opt. Soc. Am. A 7(8) 1470 (1990).
- S. Peng and G. M. Morris, "Resonant scattering from two-dimensional gratings," J. Opt. Soc. Am. A 13(5) 993 (1996).
- K. Tiefenthaler, U.S. Pat. No. 4,815,843 Mar. 28, 1989.

The contents of these documents are incorporated by reference herein.

Figure 6:
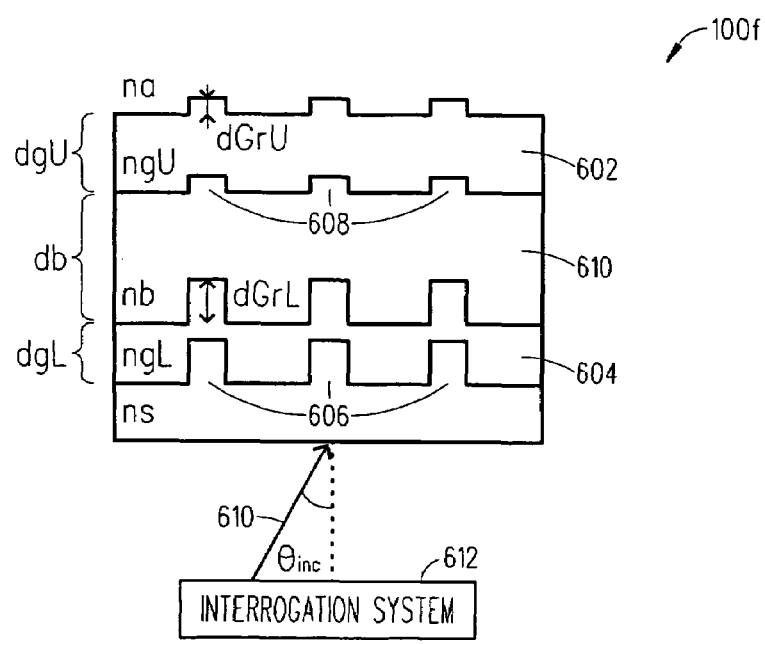
FIG. 6 is a diagram associated with a sixth embodiment of the self-referencing optical sensor in accordance with the present invention.

Referring to FIG. 6, there is a diagram associated with a sixth embodiment of the self-referencing optical sensor 100f in accordance with the present invention. The optical sensor 100f in this embodiment addresses a concern about the fabrication of dual waveguide type structures where the top (sensing) grating 602 and bottom (reference) grating 604 do not have the same depths dGrU and dGrL due to the deposition of the relatively thick buffer layer nb which can lead to a smoothing out of the sensing grating 602. The concern that occurs when the grating depth dGrU is the smaller than the grating depth dGrL is that the upper waveguide 602 has a lower alpha a than the lower waveguide 604. The problem of "alpha matching" between the two resonances of dual waveguide type structures was described in detail above with respect to optical sensor 100b (FIGS. 2A–2F).

Essentially, the alpha matching is a problem for any self-referencing waveguide grating sensor 100f (for example) that has two waveguide layers 602 and 604 where the grating depths dGrU and dGrL are different. Further, in a different index environment where the upper waveguide 602 has index ngU which is surrounded by na and nb and the lower waveguide 604 that has an index ngL which is surrounded by nb and ns this can lead to different alphas for the two waveguides 602 and 604. This problem can be solved by exploiting the fact that the grating alpha for the two polarizations TE and TM are significantly different. TM alpha is inherently much weaker than TE polarization, therefore it needs a deeper grating to achieve similar alpha in a waveguide operating in TM polarization rather than TE. As such, in the optical sensor 100f the lower grating 606 is deep, therefore it is operated in TM polarization to achieve a certain alpha. And, since the upper grating 608 is shallow due to the smoothing it can be operated in TE polarization to obtain a much stronger alpha than would be obtained for TM. In this way, one can closely match the alphas through appropriate design of the optical sensor 100f, possibly making use of a low-index buffer layer 610 (e.g., MgF has index ~1.35) to increase the index contrast between the environment of the lower waveguide 604 and the upper waveguide 602 which "sees" the analyte (index ~1.333).

A further benefit of this embodiment of the optical sensor 100f is that the resonance wavelengths can be closely spaced due to their operating in different polarizations without inducing sensitivity crosstalk which can occur for example when the lower waveguide 604 is sensitive to analyte index changes. However, a drawback of the optical sensor 100f is that the detection sensitivity in TE is lower than TM, hence the overall sensor 100f sacrifices some sensitivity when it is interrogated by an optical beam 610 emitted from an interrogation system 612.

Figure 7:
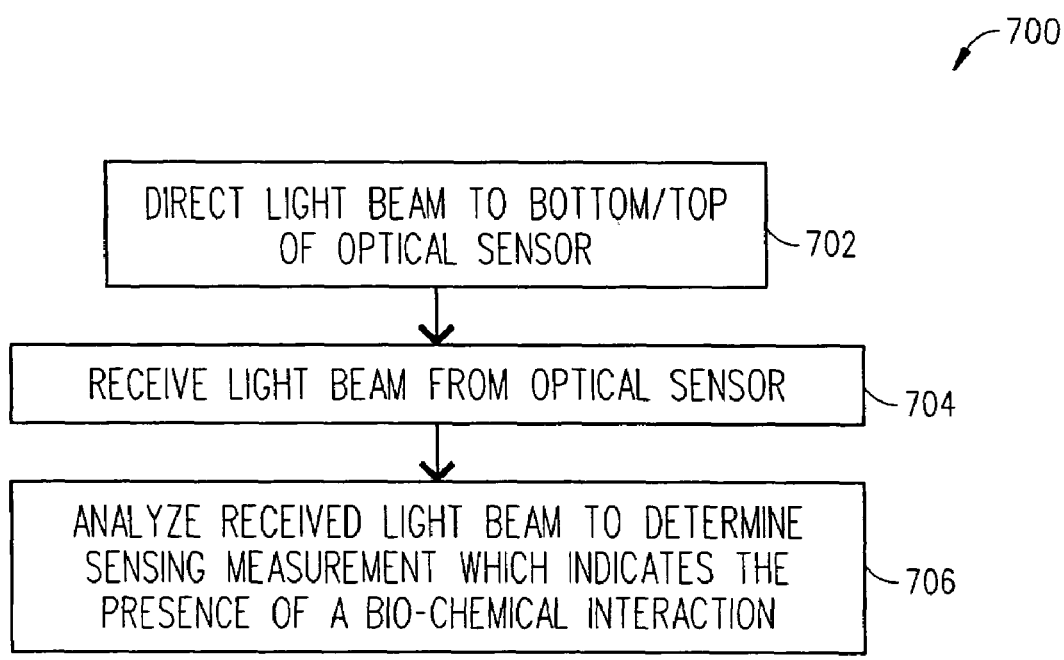
FIG. 7 is a flowchart illustrating the basic steps of a preferred method for detecting a bio-chemical interaction using any one of the self-referencing optical sensors shown in FIGS. 1–3 and 5–6.

Referring to FIG. 7, there is a flowchart illustrating the basic steps of a preferred method 700 for detecting a bio-chemical interaction using any one of the optical sensors 100a, 100b, 100c, 100e and 100f shown in FIGS. 1–3 and 5–6. Beginning at step 702, the interrogation system 116 (for example) directs a light beam 114 at the bottom (shown) or the top (not shown) of the optical sensor 100a (for example). In one embodiment, the optical sensor 100a (for example) is located within the bottom of a well in a microplate/multiwell plate. At step 704, the interrogation system 116 (for example) receives an output optical beam from the optical sensor 100a (for example). Then at step 706, a computer analyzes the output optical beam to determine a reference signal and a sensing signal which are then subtracted from one another to determine a sensing measurement which indicates whether or not the bio-chemical interaction took place in a sensing region of the optical sensor 100a (for example). It should be appreciated that any of the other optical sensors 100b, 100c, 100e and 100f can be interrogated in the same or similar manner to enable the detection of a bio-chemical interaction.

Although several embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. An athermal self-referencing optical sensor comprising:
a substrate;
a lower waveguide grating structure;
a buffer layer; and
an upper waveguide grating structure, wherein said lower waveguide grating structure has a thickness that was sized to make a rate of change of a lower resonant wavelength/temperature variation ($\Delta\lambda^L/\Delta T$) of said lower waveguide grating structure substantially equal to a rate of change of an upper resonant wavelength/temperature variation ($\Delta\lambda^U/\Delta T$) of said upper waveguide grating structure.

2. The optical sensor of claim 1, wherein when said optical sensor is interrogated then a reference signal and a sensing signal can be measured and subtracted from one another to determine a self-referenced sensing measurement which indicates whether or not a bio-chemical interaction took place in a sensing region of said upper waveguide grating structure.

3. The optical sensor of claim 1, wherein said $\Delta\lambda^L/\Delta T$ and $\Delta\lambda^U/\Delta T$ are represented by:

$$\frac{\Delta\lambda^{U,L}}{\Delta T} = \frac{\left(a^{U,L} + \frac{b^{U,L} \cdot \lambda^{U,L}}{\Lambda}\right)}{(1/\Lambda - D^{U,L})}$$

where:

$$D^{U,L} = \frac{dn_{\text{eff}}(\lambda^{U,L})}{d\lambda}$$

$$a^{U,L} = \frac{\partial n_{\text{eff}}}{\partial T}$$

$$b = \frac{d\Lambda}{dT} = \Lambda \cdot CTE$$

$\lambda^U$ is the upper resonant wavelength;
$\lambda^L$ is the lower resonant wavelength;
$\Lambda$ is the period of the lower waveguide grating structure and the upper waveguide grating structure;
$n_{\text{eff}}$ is the effective index of a waveguide mode propagation for the lower waveguide grating structure or the upper waveguide grating structure; and
CTE is the coefficient of thermal expansion for the lower waveguide grating structure or the upper waveguide grating structure.

4. A method for detecting a bio-chemical interaction in a sensing region of an optical sensor, said method comprising the steps of:
directing a light beam at the optical sensor which includes:
a substrate;
a lower waveguide grating structure;
a buffer layer; and
an upper waveguide grating structure, wherein said lower waveguide grating structure has a thickness that was sized to make a rate of change of a lower resonant wavelength/temperature variation ($\Delta\lambda^L/\Delta T$) of said lower waveguide grating structure substantially equal to a rate of change of an upper resonant wavelength/temperature variation ($\Delta\lambda^U/\Delta T$) of said upper waveguide grating structure;

receiving an output optical beam from said optical sensor; and analyzing the output optical beam to determine a reference signal and a sensing signal which are then subtracted from one another to determine a self-referenced sensing measurement which indicates whether or not the bio-chemical interaction took place in the sensing region of said optical sensor.

5. The method of claim 4, wherein said $\Delta\lambda^L/\Delta T$ and $\Delta\lambda^U/\Delta T$ are represented by:

$$\frac{\Delta\lambda^{U,L}}{\Delta T} = \frac{\left(a^{U,L} + \frac{b^{U,L} \cdot \lambda^{U,L}}{\Lambda}\right)}{(1/\Lambda - D^{U,L})}$$

where:

$$D^{U,L} = \frac{dn_{eff}(\lambda^{U,L})}{d\lambda}$$

$$a^{U,L} = \frac{\partial n_{eff}}{\partial T}$$

$$b = \frac{d\Lambda}{dT} = \Lambda \cdot CTE$$

$\lambda^U$ is the upper resonant wavelength;
$\lambda^L$ is the lower resonant wavelength;
$\Lambda$ is the period of the lower waveguide grating structure and the upper waveguide grating structure;
$n_{eff}$ is the effective index of a waveguide mode propagation for the lower waveguide grating structure or the upper waveguide grating structure; and
CTE is the coefficient of thermal expansion for the lower waveguide grating structure or the upper waveguide grating structure.

6. An athermal self-referencing optical sensor comprising:
a substrate;
an anti-resonant reflecting optical waveguide (ARROW) grating structure;
a buffer layer; and
an upper waveguide grating structure.

7. The optical sensor of claim 6, wherein:
said ARROW grating structure has a waveguide mode that operates in TE polarization; and
said upper waveguide grating structure has a waveguide mode that operates in TM polarization.

8. The optical sensor of claim 6, wherein said ARROW grating structure has a grating depth that is larger than a grating depth of said upper waveguide grating structure.

9. The optical sensor of claim 6, wherein when said optical sensor is interrogated then a reference signal and a sensing signal can be measured and subtracted from one another to determine a self-referenced sensing measurement which indicates whether or not a bio-chemical interaction took place in a sensing region of said upper waveguide grating structure.

10. A method for detecting a bio-chemical interaction in a sensing region of an optical sensor, said method comprising the steps of:
directing a light beam at the optical sensor which includes:
a substrate;
an anti-resonant reflecting optical waveguide (ARROW) grating structure;
a buffer layer; and
an upper waveguide grating structure;
receiving an output optical beam from said optical sensor; and
analyzing the output optical beam to determine a reference signal and a sensing signal which are then subtracted from one another to determine a self-referenced sensing measurement which indicates whether or not the bio-chemical interaction took place in a sensing region of said optical sensor.

11. The method of claim 10, wherein:
said ARROW grating structure has a waveguide mode that operates in TE polarization; and
said upper waveguide grating structure has a waveguide mode that operates in TM polarization.

12. The method of claim 10, wherein said ARROW grating structure has a grating depth that is larger than a grating depth of said upper waveguide grating structure.

13. An athermal self-referencing optical sensor comprising:
a substrate;
a Bragg waveguide grating structure;
a buffer layer; and
an upper waveguide grating structure.

14. The optical sensor of claim 13, wherein said substrate, Bragg waveguide grating structure, said buffer layer and said upper waveguide grating structure have predetermined refractive indices and thicknesses which ensure that during an interrogation process a wavelength shift with temperature is substantially equal for both a sensor signal and a reference signal.

15. The optical sensor of claim 13, wherein when said optical sensor is interrogated then a surface binding effect can be separated from a temperature change by solving a pair of linear equations:

$$\lambda_S = C_S \cdot \Delta t_{bio} + K_S \cdot \Delta T$$

$$\lambda_R = C_R \cdot \Delta t_{bio} + K_R \cdot \Delta T$$

where:

$$C_S = \frac{d\lambda_S}{dt_{bio}}$$

$$C_R = \frac{d\lambda_R}{dt_{bio}}$$

$$K_S = \frac{d\lambda_S}{dT}$$

$$K_R = \frac{d\lambda_R}{dT}$$

$\lambda_S$ is the sensing resonant wavelength;
$\lambda_R$ is the reference resonant wavelength; and
$t_{bio}$ is the thickness of a biological layer in which can take place a bio-chemical interaction.

16. A method for detecting a bio-chemical interaction in a sensing region of an optical sensor, said method comprising the steps of:
directing a light beam at the optical sensor which includes:
a substrate;
a Bragg waveguide grating structure;
a buffer layer; and
an upper waveguide grating structure;
receiving an output optical beam from said optical sensor; and analyzing the output optical beam to determine a reference signal and a sensing signal which are then subtracted from one another to determine a self-referenced sensing measurement which indicates whether or not the bio-chemical interaction took place in the sensing region of said optical sensor.

17. The method of claim 16, wherein said substrate, Bragg waveguide grating structure, said buffer layer and said upper waveguide grating structure have predetermined refractive indices and thicknesses which ensure that during an interrogation process a wavelength shift with temperature is substantially equal for both a sensor signal and a reference signal.

18. The method of claim 16, wherein when said optical sensor is analyzed then a surface binding effect can be separated from a temperature change by solving a pair of linear equations:

$$\lambda_S = C_S \cdot \Delta t_{bio} + K_S \cdot \Delta T$$

$$\lambda_R = C_R \cdot \Delta t_{bio} + K_R \cdot \Delta T$$

where:

$$C_S = \frac{d\lambda_S}{dt_{bio}}$$

$$C_R = \frac{d\lambda_R}{dt_{bio}}$$

$$K_S = \frac{d\lambda_S}{dT}$$

$$K_R = \frac{d\lambda_R}{dT}$$

$\lambda_S$ is the sensing resonant wavelength; and
$\lambda_R$ is the reference resonant wavelength; and
$t_{bio}$ is the thickness of a biological layer in which can take place a bio-chemical interaction.

19. An optical sensor comprising:
a substrate; and
a waveguide grating structure, wherein when said waveguide grating structure is interrogated then one can use higher mode properties of said waveguide grating structure to separate effects of a surface binding thickness ($\Delta t_{bio}$) from changes in a buffer solution refractive index ($\Delta n_{analyte}$).

20. The optical sensor of claim 19, wherein when said optical sensor is interrogated then one can separate the effects of the surface binding thickness ($\Delta t_{bio}$) from the changes in the buffer solution refractive index ($\Delta n_{analyte}$) by solving a pair of linear equations:

$$\Delta n_{eff}^{m=0} = B_0 \cdot \Delta n_{analyte} + S_0 \cdot \Delta t_{bio}$$

$$\Delta n_{eff}^{m=1} = B_1 \cdot \Delta n_{analyte} + S_1 \cdot \Delta t_{bio}$$

where:
$B_0$, $S_0$, $B_1$, $S_1$ are the bulk and surface optical field sensitivities (OFSs) for two different modes; and
$\Delta n_{eff\, for\, m=0\, and\, m=1}$ are the effective indexes of waveguide mode propagations for the waveguide grating structure.

21. A method for detecting a bio-chemical interaction in a sensing region of an optical sensor, said method comprising the steps of:
directing a light beam at the optical sensor which includes:
a substrate; and
a waveguide grating structure;
receiving an output optical beam from said optical sensor; and
analyzing said received optical beam and using higher mode properties of said waveguide grating structure to separate effects of a surface binding thickness ($\Delta t_{bio}$) from changes in a buffer solution refractive index ($\Delta n_{analyte}$) to determine whether or not the bio-chemical interaction took place in the sensing region of said optical sensor.

22. The method of claim 21, wherein when said optical sensor is analyzed then one can separate the effects of the surface binding thickness ($\Delta t_{bio}$) from the changes in the buffer solution refractive index ($\Delta n_{analyte}$) by solving a pair of linear equations:

$$\Delta n_{eff}^{m=0} = B_0 \cdot \Delta n_{analyte} + S_0 \cdot \Delta t_{bio}$$

$$\Delta n_{eff}^{m=1} = B_1 \cdot \Delta n_{analyte} + S_1 \cdot \Delta t_{bio}$$

where:
$B_0$, $S_0$, $B_1$, $S_1$ are the bulk and surface optical field sensitivities (OFSs) for two different modes; and
$\Delta n_{eff\, for\, m=0\, and\, m=1}$ are the effective indexes of waveguide mode propagations for the waveguide grating structure.

23. An optical sensor comprising:
a substrate;
a reference waveguide grating structure;
a barrier layer; and
a sensing waveguide grating structure, wherein a thickness and a refractive index of said barrier layer were determined so there is a high isolation for a quasi-guided mode of said reference waveguide grating structure and so that the quasi-guided mode is biased towards a sensing region of said sensing waveguide grating structure.

24. The optical sensor of claim 23, wherein when said optical sensor is interrogated then a reference signal and a sensing signal can be measured and subtracted from one another to determine a self-referenced sensing measurement which indicates whether or not a bio-chemical interaction took place in the sensing region of said sensing waveguide grating structure.

25. The optical sensor of claim 23, wherein:
said substrate is made from cyclo olefin;
said reference waveguide grating structure is made from $Ta_2O_5$;
said barrier layer is made from $SiO_2$; and
said sensing waveguide grating structure is made from $Ta_2O_5$.

26. A method for detecting a bio-chemical interaction in a sensing region of an optical sensor, said method comprising the steps of:
directing a light beam at the optical sensor which includes:
a substrate;
a reference waveguide grating structure;
a barrier layer; and
a sensing waveguide grating structure, wherein a thickness and a refractive index of said barrier layer were determined so there is a high isolation for a quasi-guided mode of said reference waveguide grating structure and so that the quasi-guided mode is biased towards a sensing region of said sensing waveguide grating structure;
receiving an output optical beam from said optical sensor; and
analyzing the output optical beam to determine a reference signal and a sensing signal which are then subtracted from one another to determine a self-referenced sensing measurement which indicates whether or not the bio-chemical interaction took place in the sensing region of said optical sensor.

27. The method of claim 26, wherein:
said substrate is made from cyclo olefin;
said reference waveguide grating structure is made from $Ta_2O_5$;
said barrier layer is made from $SiO_2$; and
said sensing waveguide grating structure is made from $Ta_2O_5$.

28. The optical sensor comprising:
a substrate;
a lower waveguide grating structure;
a buffer layer; and
an upper waveguide grating structure, wherein said lower waveguide grating structure has a waveguide mode that is operated in TM polarization and said upper waveguide grating structure has a waveguide mode that is operated in TE polarization.

29. The optical sensor of claim 28, wherein said lower waveguide grating structure has a grating depth that is larger than a grating depth of said upper waveguide grating structure.

30. The optical sensor of claim 28, wherein when said optical sensor is interrogated then a reference signal and a sensing signal can be measured and subtracted from one another to determine a self-referenced sensing measurement which indicates whether or not a biochemical interaction took place in a sensing region of said upper waveguide grating structure.

31. A method for detecting a bio-chemical interaction in a sensing region of an optical sensor, said method comprising the steps of:
directing a light beam at the optical sensor which includes:
a substrate;
a lower waveguide grating structure;
a buffer layer; and
an upper waveguide grating structure, wherein said lower waveguide grating structure has a waveguide mode that is operated in TM polarization and said upper waveguide grating structure has a waveguide mode that is operated in TE polarization;
receiving an output optical beam from said optical sensor; and
analyzing the output optical beam to determine a reference signal and a sensing signal which are then subtracted from one another to determine a self-referenced sensing measurement which indicates whether or not the bio-chemical interaction took place in a sensing region of said optical sensor.

32. The method of claim 31, wherein said lower waveguide grating structure has a grating depth that is larger than a grating depth of said upper waveguide grating structure.

* * * * *